(12) United States Patent
Ghigini

(10) Patent No.: US 7,527,596 B2
(45) Date of Patent: May 5, 2009

(54) ADJUSTABLE CUFF FOR MEASURING BLOOD PRESSURE

(76) Inventor: Francesca Ghigini, Via San Pietro all'Orto, 9, Milano (IT) 1-20121

(*) Notice: Subject to any disclaimer, the term of this patent is extended or adjusted under 35 U.S.C. 154(b) by 0 days.

(21) Appl. No.: 11/814,770

(22) PCT Filed: Jan. 16, 2006

(86) PCT No.: PCT/EP2006/050225

§ 371 (c)(1),
(2), (4) Date: Jul. 25, 2007

(87) PCT Pub. No.: WO2006/079593

PCT Pub. Date: Aug. 3, 2006

(65) Prior Publication Data

US 2008/0132795 A1    Jun. 5, 2008

(30) Foreign Application Priority Data

Jan. 28, 2005   (IT) .......................... MI2005A0127

(51) Int. Cl.
*A61B 5/00* (2006.01)
(52) U.S. Cl. ...................................... 600/499; 600/490
(58) Field of Classification Search .................. None
See application file for complete search history.

(56) References Cited

U.S. PATENT DOCUMENTS

| 3,935,984 | A |   | 2/1976 | Lichowsky et al. |
| 4,102,028 | A |   | 7/1978 | Currie |
| 4,429,699 | A | * | 2/1984 | Hatschek ................ 600/494 |
| 7,316,652 | B2 | * | 1/2008 | Dalgaard et al. .......... 600/499 |
| 2004/0127801 | A1 |   | 7/2004 | Takahashi et al. |

FOREIGN PATENT DOCUMENTS

| DE | 35 33 513 A1 | 4/1987 |
| EP | 1 013 220 A1 | 6/2000 |

OTHER PUBLICATIONS

Translation of EP 1013220.*

* cited by examiner

Primary Examiner—Robert L Nasser
(74) Attorney, Agent, or Firm—Lowrie, Lando & Anastasi, LLP

(57) ABSTRACT

A cuff (1) for measuring arterial pressure including a tubular sleeve (2) with an integrated inflatable chamber (11), which is adapted to be wrapped around the arm of a patient; the cuff includes fastening means (10) adapted to fasten the cuff (1) around the arm of the patient and to detect the circumference of the arm, in order to use the circumference datum as a connection factor for measuring the arterial pressure detected by means of the cuff (1).

5 Claims, 3 Drawing Sheets

ADJUSTABLE CUFF FOR MEASURING BLOOD PRESSURE

FILED OF THE INVENTION

The present invention relates to a cuff for measuring blood pressure. More particularly, the invention relates to a cuff adapted to compensate for differences among individuals in the size of the arm on which the pressure is measured, so that such differences cannot affect the result of the measurement.

BACKGROUND OF THE INVENTION

As it is known, blood pressure is measured by using an instrument which is composed of a pressure gage connected to a cuff with a chamber which can be inflated by means of a bulb, so as to oppose a known pressure to the arterial pressure and therefore allow to read pressure values when blood flow is detected, by listening with a stethoscope during decompression of the cuff and subsequently the level at which the action of the cuff no longer affects the detected sounds.

The inflatable chamber, integrated in the cuff applied to the arm of the patient, produces on the arm a pressure which, at a certain point of the compression, exceeds the arterial pressure, interrupting the blood flow downstream of the cuff.

Once the arterial pressure has been exceeded by 20-30 mm Hg, decompression of the cuff is performed by means of a pneumatic valve integrated in the bulb.

During decompression, the operator listens to the sounds produced by the artery by using a stethoscope which is conveniently placed on the arm. In this manner, the operator detects a series of sounds having different intensities, durations and tones, produced by the arterial pulses, which in turn are generated by cardiac activity and by the resistance of the arterial vessel.

The operator must determine which of these pulses represents the systolic value and which one represents the diastolic value.

However, the procedure described above can be influenced by errors, one of which is that cuffs are usually used which are not proportionate to the circumference of the arm, and this introduces an error which alters the measurement.

In this regard, there is extensive medical literature which agrees in deeming that it is incorrect to use a single cuff regardless of arm size, and in deeming that when the circumference of the arm increases it is necessary to use larger cuffs and, vice versa, arms having a smaller circumference require the use of smaller cuffs. There is unanimous judgment regarding the fact that using the same cuff leads to an overestimation of the values for arms of the former type and an underestimation for arms of the latter type. Although currently there is no unanimous agreement in determining the measurement of the error that is introduced, it is found that this error is certainly substantial and such as to induce, in many cases of people with arms having a larger circumference, the prescription of an antihypertension therapy which is harmful for the patient and expensive for the public, or an underestimation of hypertension of patients with a small arm circumference.

On the other hand, the use of several cuffs is, from the point of view of medical practice, a solution which is difficult to provide, due to the consequent need of the doctor to have and carry with him a bulky set of various cuffs and due to the increase in the time required to measure the pressure, since in each instance it is necessary to measure the circumference of the arm and then apply the most suitable cuff.

Moreover, the correction could not be absolute, since it is evidently not possible to have a set of cuffs of so many sizes as to ensure the same measurement precision for each arm diameter.

SUMMARY OF THE INVENTION

The aim of the present invention is to provide a cuff for measuring arterial pressure which while wrapping around the arm detects its circumference, making this datum available in order to introduce a correction factor which is correlated with said datum, so as to provide more reliable measured pressure results.

Within this aim, an object of the present invention is to provide a cuff for measuring arterial pressure which allows to detect automatically the circumference of the arm around which the cuff is arranged.

Another object of the present invention is to provide a cuff for measuring arterial pressure which is highly reliable, relatively simple to provide and at competitive costs.

This aim and these and other objects, which will become better apparent hereinafter, are achieved by a cuff for measuring arterial pressure, which comprises a tubular sleeve with an integrated inflatable chamber, which is adapted to be wrapped around the arm of a patient, characterized in that it comprises fastening means adapted to fasten the cuff around the arm of the patient and to detect the circumference of said arm, in order to use the circumference datum as a correction factor for measuring the arterial pressure detected by means of said cuff.

BRIEF DESCRIPTION OF THE DRAWINGS

Further characteristics and advantages of the invention will become better apparent from the following detailed description of a preferred but not exclusive embodiment of the cuff according to the present invention, illustrated by way of non-limiting example in the accompanying drawings, wherein.

DETAILED DESCRIPTION OF THE INVENTION

Figure 1:
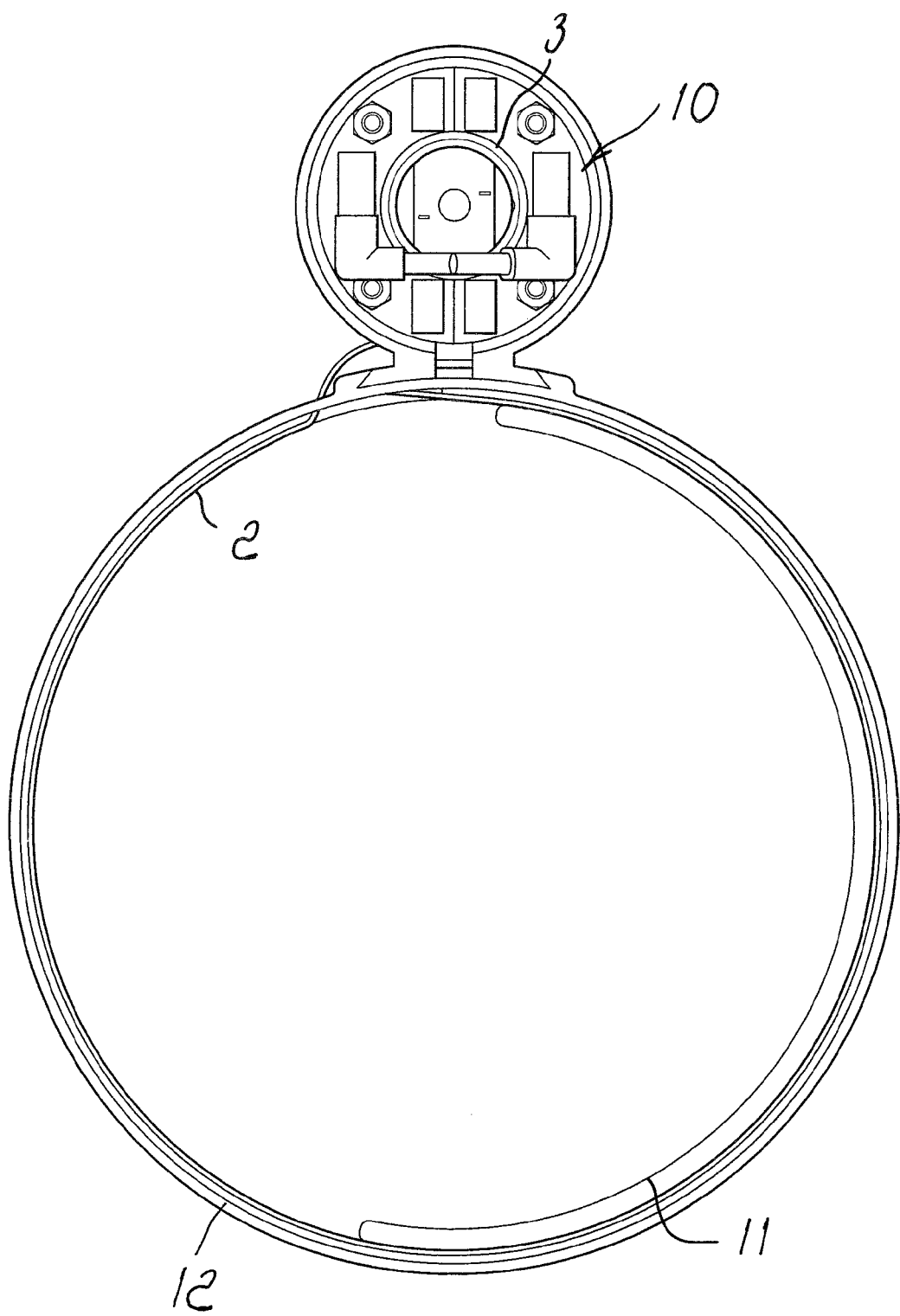
FIG. 1 is a front view of a first embodiment of the cuff according to the present invention.

With reference to the figures, a cuff according to the present invention, generally designated by the reference numeral 1, comprises a tubular sleeve 2, provided with an integrated inflatable chamber 11, which is adapted to be wrapped around the arm of a patient. Conveniently, the sleeve is provided with fastening means.

The fastening means are constituted for example by a winding roller 10, which is adapted to wind the tubular sleeve 2 on itself.

Conveniently, the sleeve is constituted for example by a nylon band, inside which the inflatable chamber 11 is arranged.

Figure 2:
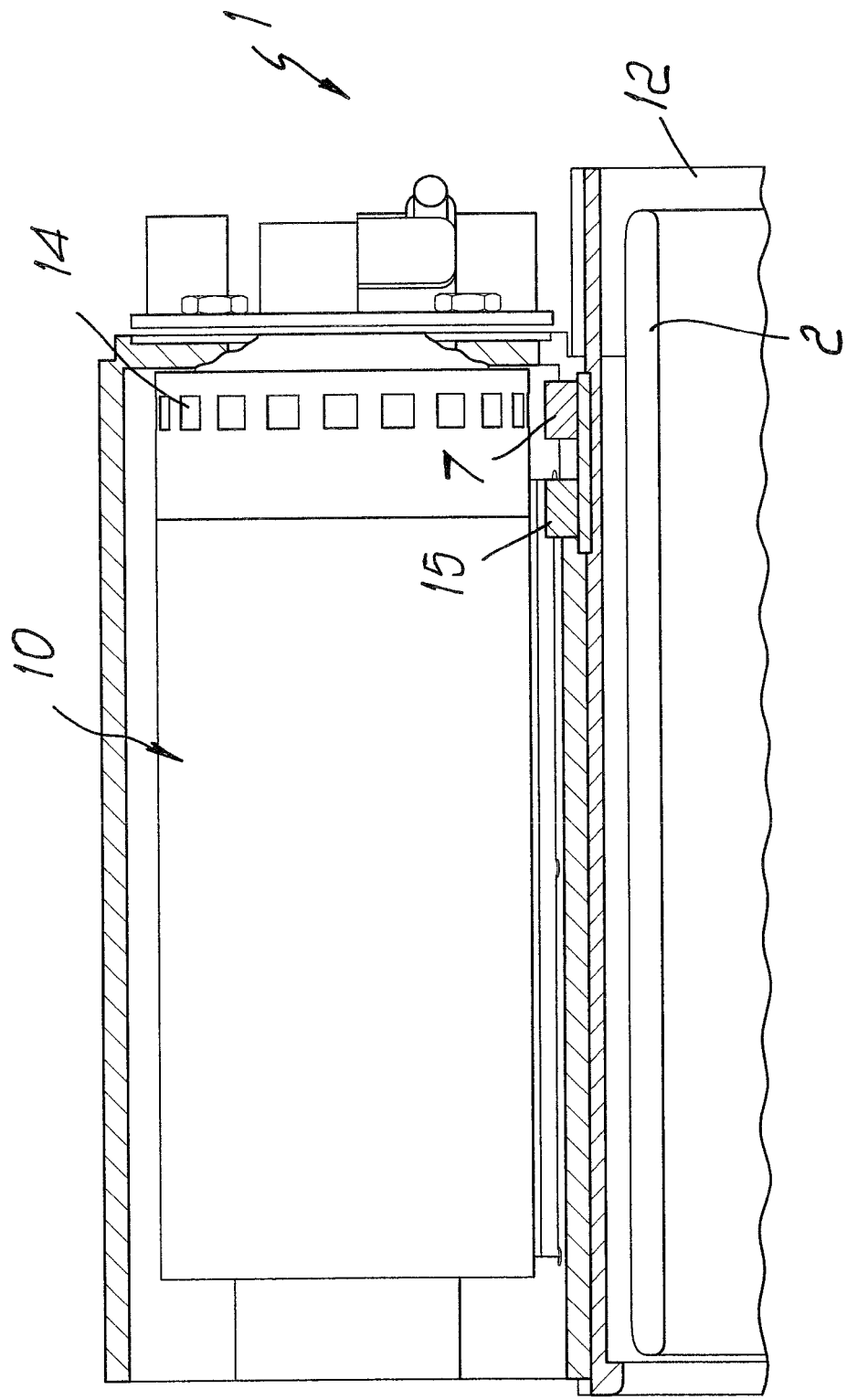
FIG. 2 is a sectional view of a detail of the cuff of FIG. 1.

In the embodiment of FIGS. 1 and 2, the tubular sleeve is protected by an outer enclosure 12, which encloses it and acts as a support for the winding means.

The winding roller is actuated by a gearmotor 3 and has, at an end portion, a reflective band 13 with positioning notches 14, which are adapted to be read by sensor means which comprise, for example, a photocell 7, which accordingly detects the degree of winding of the tubular sleeve 2 around the arm of the patient and therefore detects indirectly a measurement of the circumference of the arm of the patient.

Additional sensor means 15 detect a stroke limit position.

Figure 3:
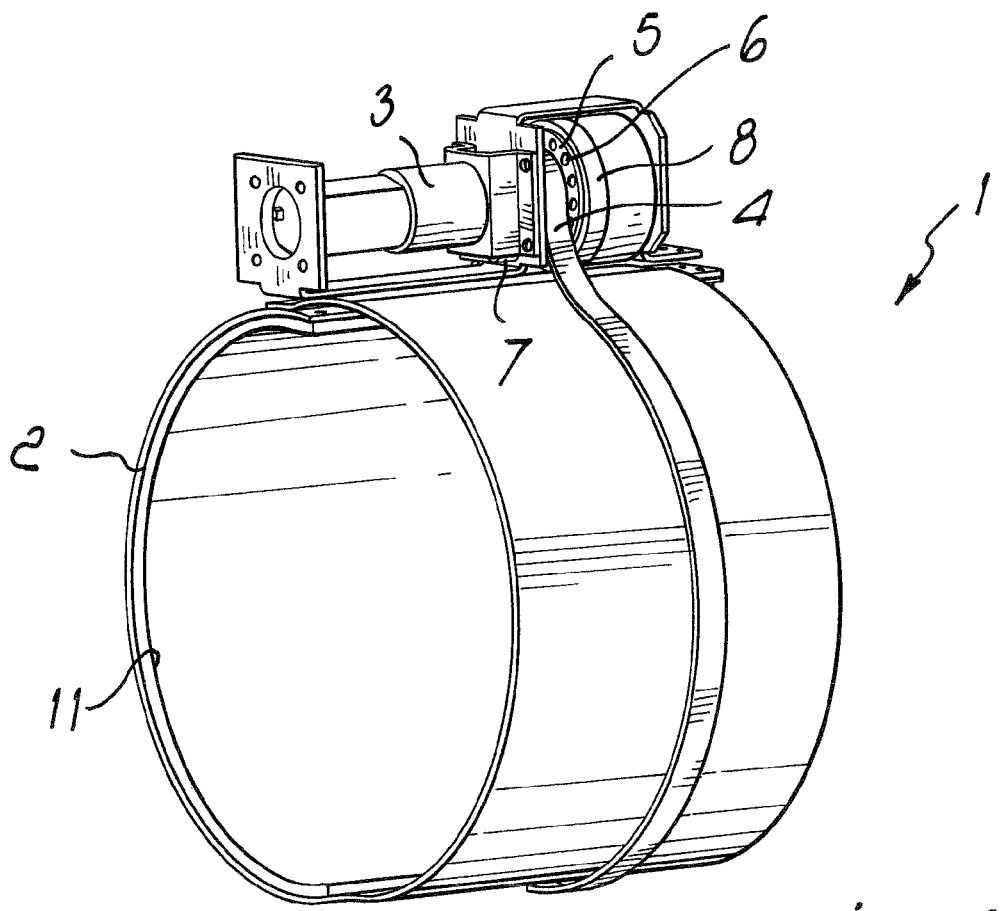
FIG. 3 is a perspective view of a second embodiment of the cuff according to the present invention.
Figure 4:
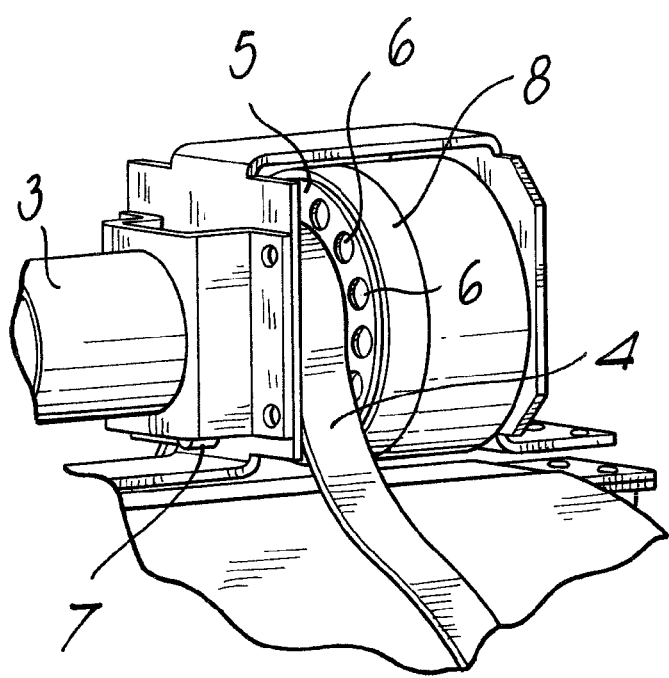
FIG. 4 is a perspective view of a detail of the cuff shown in FIG. 3.

In the second embodiment of the invention, shown in FIGS. 3 and 4, the fastening means are constituted conveniently by the gearmotor 3, which is adapted to wind up a toothed belt 4, which is arranged around the circumference of the tubular sleeve 2; as a consequence of the rotation of the gearmotor 3, the belt 4 tightens around the tubular sleeve 2, adapting its circumference to the circumference of the arm around which the sleeve is wrapped. Conveniently, the gearmotor supports a circular element 5, which is provided with suitable notches 6 which are adapted to constitute an indication of the winding of the belt 4 and therefore, indirectly, of the circumference of the arm of the patient.

The fastening means are connected externally to the surface of the tubular sleeve 2.

The sensor means 7, constituted conveniently for example by a photocell, detect the number of notches 6 of the circular element 5, so as to determine the degree of winding of the belt 4 and therefore, as mentioned, the circumference of the arm of the patient.

The gearmotor is provided with a brake 8, which is adapted to keep the belt wound when winding stops.

In both embodiments, the measurement of the circumference of the arm, performed indirectly by the photocell 7, is used as a datum to correct the pressure value measured by the gage, by applying for example an algorithm provided according to the prescriptions determined by medical doctrine, in order to compensate for differences arising from the subjective characteristics of the arm of the patient.

The corrective factor obtained from this algorithm can be modified on the basis of anthropometric studies. The operation of the cuff according to the invention is as follows.

First of all, the operator places the cuff 1 around the arm of the patient whose arterial pressure he wishes to measure and then, by operating the gearmotor 3, actuates the winding roller 10 in order to fasten the sleeve 2 around the arm of the patient or, in the second embodiment, tightens the toothed belt 4 around the sleeve 2 and therefore around the arm of the patient. The winding of the belt and therefore the fastening force thereof against the sleeve 2, or the fastening force of the sleeve 2 around the arm of the patient, is rendered constant for all arms by controlling the force applied by the motor. During the winding of the cuff, the circumference of the arm of the patient is measured indirectly by means of the photocell 7, which detects the number of notches of the winding roller 10 or of the rotating disk 5, which is rigidly coupled to the gearmotor shaft, which have passed below said photocell.

Detection of the winding of the sleeve 2 or of the sliding of the belt 4 therefore allows to determine the circumference of the arm of the patient and to introduce this datum as a corrective factor for measuring arterial pressure, consequently indicating on an electronic pressure gage the pressure values corrected as a function of the size of the arm. The measurement is therefore performed normally by means of the cuff 1 and the accessories connected to the cuff, i.e., an electronic pressure gage, the bulb which allows to inflate the chamber integrated in the cuff, and the stethoscope used to detect the sounds produced by the artery of the arm of the patient.

The cuff according to the invention may further be provided with a display which is adapted to visualize the detected pressure information, with and without the corrective factor. This allows to check the indicated values.

In practice it has been found that the cuff according to the invention fully achieves the intended aim and objects, since it allows to measure automatically the size of the arm of the patient and to use this datum to correct the pressure measurement subsequently acquired. Substantially, with a single cuff the doctor is capable of performing a correct measurement of the blood pressure of patients having different arm circumferences.

The cuff thus conceived is susceptible of numerous modifications and variations, all of which are within the scope of the appended claims; all the details may further be replaced with other technically equivalent elements.

In practice, the materials used, as well as the contingent shapes and dimensions, may be any according to requirements and to the state of the art.

The disclosures in Italian Patent Application No. MI2005A000127 from which this application claims priority are incorporated herein by reference.

The invention claimed is:

1. A cuff for measuring arterial pressure, comprising a tubular sleeve with an integrated inflatable chamber, which is adapted to be wrapped around an arm of a patient, the cuff comprising fastening means adapted to fasten the tubular sleeve around the arm of the patent and to detect the circumference of said arm, the fastening means comprising a gearmotor adapted to drive a winding roller, which winds the sleeve around it, characterized in that the winding roller is provided with a series of notches which can be detected by sensor means oriented radially with respect to the notches, in order to give an indication of the degree of winding of the sleeve around the arm of the patient to detect the circumference.

2. The cuff according to claim 1, characterized in that said sensor means comprise a photocell.

3. The cuff according to claim 1, characterized in that the cuff comprises means for measuring arterial pressure and compensating the pressure measurements according to the datum of the winding of the sleeve on the winding roller, acquired by the sensor means.

4. The cuff according to claim 1, characterized in that the notches are arranged at an end portion of the winding roller.

5. The cuff according to claim 1, characterized in that the notches are arranged on a reflective band.

* * * * *